US007074984B2

(12) United States Patent
Kermicle et al.

(10) Patent No.: US 7,074,984 B2
(45) Date of Patent: Jul. 11, 2006

(54) CROSS-INCOMPATIBILITY TRAITS FROM TEOSINTE AND THEIR USE IN CORN

(75) Inventors: Jerry L. Kermicle, Cross Plains, WI (US); Matthew M. S. Evans, Madison, WI (US); Steven R. Gerrish, Elkhorn, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/821,879

(22) Filed: Mar. 30, 2001

(65) Prior Publication Data

US 2002/0069435 A1    Jun. 6, 2002

Related U.S. Application Data

(60) Provisional application No. 60/193,082, filed on Mar. 30, 2000.

(51) Int. Cl.
*A01H 1/00* (2006.01)
*A01H 1/02* (2006.01)

(52) U.S. Cl. ............... 800/275; 800/267; 800/269; 800/271; 800/273

(58) Field of Classification Search ............... 800/269, 800/266, 271, 273, 274, 275, 320.1, 267; 435/6
See application file for complete search history.

(56) References Cited

FOREIGN PATENT DOCUMENTS

RU    2032320    4/1995

OTHER PUBLICATIONS

Goldman et al. Crop Sci. 34(4): 908-615, 1994.*
Rashid et al. J. Heredity 83(2): 130-134, 1992.*
Nelson, O. pp. 496-503 In: The Maize Handbook, Freeling et al. eds., Springer-Verlag: New York, 1994.*
Ashman, R. B. Maize Genetics Coop. News-letter 55:50-51, Mar. 1981.*
Branch: et al. Genetica Agranà 22(4): 345-361, 1970.*

Kermicle, J.L., et al.: "*Cross-incompatibility* between maize and teosinte" MAYDICA, (1990) vol. 35, No. 4, pp. 399-408 XP001031166 the whole document.
Evans, M.M.S., et al.: "Teosinte crossing barrier 1, a locus governing hybridization of teosinte with maize" Theoretical and Applied Genetics, (2001) vol. 103, No. 2/3, pp. 259-265., XP002181800; the whole document.
Database Cab 'Online!' Cab International, Wallingford, Oxon, GB AN 84:71930 Shmaraev, G.E., et al.: "Hybridization of maize with teosinte" XP002191801 abstract & Vestnik Se'skokhozyaistvennoi Nauki, (1981) No. 5, pp. 46-52. 31.
Database Biosis 'Online!' Biosciences Information Service, Philadelphia, PA, US: 1992 Rashid A. et al: "The RSS System of Unideirectional Cross-Incompatibility in Maize I. Genetics" Database accession No. PREV199294017089 XP002181802 abstract & Journal of Heredity, vol. 83, No. 2, 1992, pp. 130-134, ISSN 0022-1503.
Database Biosis Online! Biosciences Information Service, Philadelphia, PA, US; 1983 Sukhapinda K. et al.: "Nonreciprocal Partial Cross Incompatibility in Maize Zea-Mays" Database accession No. PREV198376084928 XP002181803 abstract & Canadian Journal of Genetics and Cytology, vol. 25, No. 3, 1983, pp. 270-277, ISSN: 0008-4093.
Jerry Kermicle, "Cross Compatibility with the genus Zea" in Serratos, J.A., M.C. Willcox, and F. Castillo-Gonzales (eds. ). 1997. Gene Flow Among Maize Landraces, Improved Maize Varieties, and Teosinte: Implications for Transgenic Maize. Mexico, D.F. CIMMYT which was presented at a conference in El Batan, Mexico on Sep. 21-25, 1995.

* cited by examiner

*Primary Examiner*—David T. Fox
(74) *Attorney, Agent, or Firm*—Wood, Phillips, Katz, Clark & Mortimer (57) ABSTRACT

The present invention relates to a teosinte crossing barrier trait. Plants containing said trait exhibit the phenotype of cross-incompatiblity. The present invention also relates to new cross-incompatible plants, including inbred, hybrid, haploid, apomictic and/or genetically engineered plants, containing the teosinte crossing barrier trait and exhibiting commercially desirable characteristics.

1 Claim, 5 Drawing Sheets

[1] The designation *tcb* as used herein means the absence of the silk effect function and the pollen effect function (TIC-CP2). *tcb* has been found in all maize tested to date.

CROSS-INCOMPATIBILITY TRAITS FROM TEOSINTE AND THEIR USE IN CORN

CROSS-RELATED APPLICATION INFORMATION

This application claims priority from U.S. application Ser. No. 60/193,082 filed on Mar. 30, 2000.

STATEMENT OF GOVERNMENT RIGHTS

This invention was made with United States government support awarded by the following agencies: USDA 98-CRHF-0-6055.

TECHNICAL FIELD OF THE INVENTION

The present invention relates to a teosinte crossing barrier trait. Plants containing said trait exhibit the phenotype of cross-incompatiblity. The present invention also relates to new cross-incompatible plants, including inbred, hybrid, haploid, apomictic and/or genetically engineered plants, containing the teosinte crossing barrier trait. The cross-incompatible plants containing the teosinte crossing barrier trait described herein can be used in commercial fields to prevent the indiscriminate hybridization of these plants from undesired lines, such as from genetically engineered plants.

BACKGROUND OF THE INVENTION

Maize (*Zea mays* L.), also known as corn, is a major worldwide crop that has a number of practical uses. Maize is used as a food source for both humans and animals as well as a source of carbohydrates, oil, protein and fiber. Many products are produced or extracted from maize, such as corn syrup, adhesives, food thickeners, industrial and medical absorbants, ethanol, as well as many other products.

Maize can be bred by self-pollination or cross-pollination. Maize has separate male (called the tassel) and female (called the ear) inflorescences on the same plant. Maize is naturally pollinated when wind blows pollen from the tassels to the silks that protrude from the tops of the developing ears.

Most maize is produced from hybrid seed. The production of hybrid maize seed requires the elimination or inactivation of pollen produced by the female parent. Incomplete removal or inactivation of the pollen provides the potential for self-pollination. This inadvertently self-pollinated seed may be unintentionally harvested and packaged with hybrid seed. Several methods have been developed which can be used to control male fertility and thus prevent self-pollination. These methods include manual or mechanical emasculation (commonly referred to as detasseling), cytoplasmic male sterility, genetic male sterility, gametocides and the like.

Most frequently, hybrid maize seed is produced by manual or mechanical detasseling. This method works as follows. Typically, alternate strips of two inbred varieties of maize are planted in a field and the pollen-bearing tassels are removed from the inbred which is to be used as the female, prior to pollen being shed. As long as there is sufficient isolation from sources of foreign maize pollen, the ears of the detasseled inbred will be fertilized only from the male inbred, and the resulting seed is a hybrid.

One of the problems with detasseling is that it is laborious (and hence expensive) and is sometimes, unreliable. One alternative, to detasseling involves the use of cytoplasmic male sterile (CMS) inbreds. Cytoplasmic male sterility is governed by factors in the maternal cytoplasm that induce sterility. Cytoplasmic male sterility can be used for reproduction of the female by fertilization with fertile pollen (i.e., from a plant which is not cytoplasmically male sterile).

Another alternative to detasseling involves the use of genetic male sterility. Genetic male sterility is governed by nuclear factors that induce sterility and inhibit the normal development of the anthers and pollen. Genetic male sterility is inherited according to Mendelian principles in which the alleles for sterility are recessive (ms) to the alleles for pollen fertility (MS). There are many methods for conferring genetic male sterility. For example, U.S. Pat. Nos. 4,654,465 and 4,727,219 disclose the use of multiple mutant genes at separate locations within the genome to confer male sterility. U.S. Pat. Nos. 3,861,709 and 3,710,511 describe the use of chromosomal translocations for conferring genetic male sterility. Other methods involve delivering into a plant a gene encoding a cytotoxic substance associated with a male tissue specific promoter or an antisense system in which a gene critical to fertility is identified and an antisense to that gene inserted in the plant (see EP 329 308 and WO 90/08828).

Another alternative to detasseling is the application of certain chemicals referred to as gametocides, pollen suppressants or chemical hybridizing agents. These chemicals block or kill viable pollen formation and hence produce a transitory male sterility. However, there are a number of factors which affect the usefulness of these chemicals such as the expense of the chemicals, genotype specificity and the time of the application.

Homozygous inbred maize lines are required from the production of maize hybrids. Homozygous inbred lines can be produced via pedigree breeding, where two maize inbred lines, each of which possesses different sets of desirable characteristics, are crossed. Superior plants are selected for the traits of interest and then selfed for a number of generations in order for the line to become increasingly inbred. This process of continued selfing and selection is continued for five or more generations. The result of such breeding is the production of lines which are genetically homogenous or inbred. Typically, the development period for an inbred line using this method is a minimum of five years, if not longer.

One way for reaching homogeneity more quickly or completely when developing an inbred line is through the use of haploid plants. Haploids are plants which contain only one-half of the chromosome number present in somatic cells, which are cells other than haploid cells. There are a few maize plants which are known to generate haploids spontaneously. For example, plants are known which possess an indeterminate gametophyte (ig) gene which generate haploids. Additionally, a line known as 'Stock 6' (See, Birchler, J. A., "Practical Aspects of Haploid Production," *The Maize Handbook*, Freeling and Walbot (eds). pp. 386–388 (1996)) possesses a propensity to generate haploids. Utilization of either ig or 'Stock 6' in a cross will result in the production of some haploid plants in the progeny.

Alternatively, haploid plants can be produced using techniques known in the art. One such technique is anther culture. Anther culture is a method by which large numbers of haploids can be produced directly from anthers in vitro. Generally, anther culture involves isolating immature anthers from plants and placing them onto a medium which induces the cells within the anther, which would normally be destined to become pollen grains, to begin dividing and form a cell culture from which the haploid plants can be regenerated. A number of techniques for carrying out anther culture are known in the art and are disclosed in J. M. Dunwell, "Anther and Ovary Culture", In S W J Bright and M G K Jones, (eds.), Cereal Tissue and Cell Culture, Martinus Nijhoff Publisher, 1985, Dordrecht, pp. 1–44 and U.S. Pat. Nos. 5,306,864, 5,322,789 5,445,961, and 5,602, 310. Another method which can be used to produce haploids is microspore culture. Microspore culture is similar to anther culture except that microspores are used instead of anthers to produce haploid plants (See, Coumans, et al., *Plant Cell Reports* 7:618–621 (1989); Pescitelli et al., *Plant Cell Reports,* 7:673–676 (1989)). The advantage of anther or microspore culture is that it makes it possible to test a larger number of new mutations and gene combinations and to select among those for desirable traits.

Haploids obtained either spontaneously or from anther or microspore culture, are sterile. To remedy this sterility, the chromosome number of the haploid can be doubled. Sometimes, the chromosome doubling can occur spontaneously. However, many times an agent must be used to effect the chromosome doubling. Agents which can be used to effect such chromosome doubling, include, but are not limited to, colchicine or a mitotic spindle inhibitor. The doubling of the chromosome number results in doubled haploid plants which are completely fertile and inbred. Because these doubled haploid plants breed true, it makes the selection process for desirable traits more efficient. Such doubled haploid plants possessing desirable traits or characteristics can be used in pedigree breeding to produce commercially valuable hybrids.

There exists a number of different methods for introducing a desired trait or characteristic into a targeted maize germplasm source, whether such maize germplasm source is an inbred or hybrid plant.

In a one method, backcrossing is used to introduce a desired trait or characteristic into a targeted maize germplasm source (called a recurrent parent) by crossing the recurrent parent with a donor plant (which is not the recurrent parent) which expresses certain traits of interest, such as, but not limited to, disease resistance, high yield potential, good stalk strength, reasonable drought tolerance, etc. While the donor plant is preferably an inbred, it can also be any plant variety which is cross-fertile with the recurrent parent. The progeny resulting from this crossing are then backcrossed to the recurrent parent, progeny possessing desirable traits identified, and the process repeated. The process of backcrossing to the recurrent parent and selecting for the desired traits is repeated for five or more generations. The progeny resulting from this process are homozygous for loci controlling the trait(s) being transferred but will be like the recurrent parent. The last backcross generation is then selfed in order to provide for pure breeding progeny for the gene(s) being transferred.

In a second method, apomixis can be used to introduce a desired trait or characteristic into a targeted maize germplasm source. Apomixis involves the production of hybrid seed without sexual reproduction. Apomixis is a natural method of reproduction in some plants and results in offspring that are genetically identical (i.e. clones) to the mother plant, thus allowing improved hybrids, to breed true. This would permit commercial producers and resource-poor farmers to replant seeds they produce, a strategy not practical with hybrid varieties available today for crops such as maize. U.S. Pat. No. 5,710,367, herein incorporated by reference, describes apomictic maize that have two unidentified genes which are believed to control apomictic development of the egg, as well as certain methods for making apomictic maize.

In a third method, genetic engineering can be used to introduce a desired trait or characteristic into a targeted maize germplasm source. Genetic engineering refers to the sophisticated, artificial techniques which are used to transfer genes from one organism to a recipient organism. In agriculture, genetic engineering is used to create new plant varieties containing genes from other organisms which provide the recipient plant with improved traits, such as, but not limited to, improved yield, color, height, tolerance to frost, insect or disease resistance. However, there has been a great deal of apprehension about the release of genetically engineered plants into the environment. In the United States, the U.S. Department of Agriculture, the Food and Drug Administration and the Environmental Protection Agency, all regulate the use of genetically engineered organisms, including genetically engineered plants.

One of the biggest concerns regarding genetically engineered or genetically modified (hereinafter "GM") crops involves the possible contamination of non-GM crops by GM crops. Specifically, there is concern that transgenes contained in GM crops will travel, either through pollen or seed, to adjoining fields where non-GM crops are being cultivated and pollinate the non-GM crops. This so-called "pollen contamination" or "indiscriminate hybridization" can be costly to a farmer engaged in farming using non-GM crops. Crop isolation distances, crop rotational and management practices have been developed in an effort to alleviate the problem of "pollen contamination". For example, in the U.S., it is recommended that an isolation distance of 203.1 meters (about 0.126 miles) be established between GM and non-GM maize fields for the purposes of seed production. The presence of natural barriers can be used to reduce this isolation distance.

Thereupon, it is readily apparent that cross-pollinating plants, such as maize, require a mechanism for preventing indiscriminate hybridization, especially from GM plants. Although differences in timing and isolation distance may contribute to reproductive isolation, physiological barriers often are sufficient to prevent crossing, especially among wind-pollinated species. One such possible mechanism for preventing such indiscriminate hybridization is cross-incompatibility. However, in contrast to self-incompatibility, cross-incompatibility (hereinafter referred to as "CI") is poorly characterized both genetically and physiologically.

In domesticated maize, CI ranges in degree from creating a preference among pollen classes up to preventing seed set. Genes responsible for these effects are called gametophyte factors (hereinafter "Ga") because the efficiency of pollen function is affected (see Nelson, O. E., *The Maize Handbook*, M. Freeling and V., Walbot, eds. Springer-Verlag (1993)). Ga factors conferring only a preference among pollen genotypes are cryptic, influencing the transmission of linked genes and the competitive ability of pollen in mixtures. Examples that involve recognition between corresponding alleles in pollen and silks are Ga2, Ga4, Ga8, and certain combinations involving Ga1. Incompatibility leading to failure of seed set occurs in conjunction with the strong allele of Gal, specifically when Ga1-s Ga1-s plants are pollinated with ga1 ga1, the cross used to isolate commercial popcorn from the pollen of other maize plants. As a system of isolation, Ga1-s is imperfect because some maize strains carry a ga1 -s or yet another allele, Ga1-m, which permits them to cross to strains containing both ga1 and Ga1-s. In these strains, the barrier breaks down.

Thereupon, there is a need in the art for genetically and physiologically well-characterized cross-incompatibility systems in maize which prevent the indiscriminate hybridization of maize plants from unwanted pollen sources.

SUMMARY OF THE INVENTION

The present invention relates to a cross-incompatible maize plant containing a teosinte crossing barrier ("TCB") trait. A cross-incompatible maize plant containing the TCB trait plant (1) fails to set seed when pollinated by plants lacking the TCB trait but sets seed when pollinated by plants carrying the TCB trait; and/or (2) maintains functional pollen and sets seed when pollinated by itself or causes other maize plants to set seed when pollinated by said plant. In addition to the TCB trait, the cross-incompatible maize plants of the present invention further comprise a gene cluster within its genome wherein said gene cluster is located on the short arm of chromosome 4 between map units 40–85. The gene cluster of the present invention comprises (1) a Tcb locus within its genome; and/or (2) at least one modifier gene within its genome. The Tcb locus is located on the short arm of chromosome 4 about 6 map units distal to the sugary1 gene and bout 40 map units from the Ga1 gene. The cross-incompatible maize plants of the present invention can be inbred, hybrid, haploid, apomictic and/or genetically engineered plants.

The present invention further relates to a cross-incompatible maize plant exhibiting a TCB trait wherein said TCB trait is derived from W22-TCB. Such a cross-incompatible maize plant can further contain a gene cluster within its genome wherein said gene cluster is located on the short arm of chromosome 4 between map units 40–85. The gene cluster can contain (1) a Tcb locus within its genome; and/or (2) at least one modifier within its genome. The cross-incompatible maize plant of the present invention can be an inbred, hybrid, haploid, apomictic and/or and genetically engineered plant.

The present invention further relates to a process for obtaining a first inbred maize plant, which when crossed with a second inbred maize plant, produces hybrid maize seed, which when planted and grown under plant growth conditions, produces hybrid maize plants which exhibit the TCB trait of cross-incompatibility. The first step of the process involves selecting a first donor parental maize plant from a population of maize plants which are cross-incompatible and contain a TCB trait. The second step involves crossing the selected donor first parental maize plant with a second parental maize plant. The second parental maize plant preferably contains genes which encode for desirable traits in hybrid combination. In addition, the second parental maize plant may or may not be cross-incompatible and contain the TCB trait. The third step involves collecting the resulting maize seed. The fourth step involves planting and growing the resulting seed under plant growth conditions. The fifth step involves screening the resulting plant population for the presence of the TCB trait identified in the first step. The final step involves selecting plants from said population containing the TCB trait for cross-incompatibility for further crossings and screenings until a maize line is obtained which is homozygous for the TCB trait so as to provide this trait in an inbred to be used in hybrid combination. Cross-incompatible inbred maize plants containing the TCB trait produced as a result of this process are also encompassed by the present invention.

The present invention further relates to a process of producing a cross-incompatible hybrid maize plant containing a TCB trait. The first step of the process involves crossing a cross-incompatible inbred maize plant containing the TCB trait for cross-incompatibility with a second maize inbred line to produce a segregating plant population. Preferably, the second maize inbred line contains genes encoding desirable phenotypic traits. In addition, the second maize inbred line may or may not be cross-incompatible and contain the TCB trait. The second step of the process involves collecting the resulting hybrid maize seed. The present invention also relates to a cross-incompatible hybrid maize plant containing a TCB trait produced as a result of this process.

The present invention further relates to a process for selecting a first donor parental maize plant suitable for use in producing an inbred maize plant, which inbred maize plant, if crossed with a second inbred maize plant, produces a hybrid maize plant which is cross-incompatible and contains a TCB trait. The method involves the step of analyzing each plant from a population of maize plants for plants containing a TCB trait. The method can further involves the steps of analyzing the DNA of each plant from the population of maize plants for a gene cluster within each plant's genome wherein said gene cluster is located on the short arm of chromosome 4 between map units 40–85. Additionally, the DNA of each plant from the population of maize plants can be further analyzed for: (1) a Tcb locus located on the short arm of chromosome 4 about 6 map units distal to the sugary1 gene and about 40 map units from the gene Ga1 gene; and/or (2) at least one modifier gene. The present invention also relates to a cross-incompatible first donor parental maize plant containing a TCB trait produced as a result of this process.

The present invention further relates to a process for selecting a cross-incompatible hybrid maize plant containing a TCB trait. The method involves the step of analyzing each plant from a population of hybrid maize plants for the TCB trait. The method can further involves the steps of analyzing the DNA of each plant from the population of maize plants for a gene cluster within each plant's genome wherein said gene cluster is located on the short arm of chromosome 4 between map units 40–85. Additionally, the DNA of each plant from the population of maize plants can be further analyzed for: (1) a Tcb locus located on the short arm of chromosome 4 about 6 map units distal to the sugary1 gene and about 40 map units from the gene Ga1 gene; and/or (2) at least one modifier gene. The present invention also relates to a cross-incompatible hybrid maize plant containing a TCB trait produced as a result of this process.

The present invention further relates to a process of controlling hybridization of a maize plant in a field and/or a phytotron or greenhouse. The process involves the step of planting in a field and/or phytotron or greenhouse a cross-incompatible maize plant containing the previously described TCB trait.

The present invention further relates to a process of controlling hybridization of inbred maize plants in a field being used in hybrid seed production. The process involves the step of planting in a field and/or a phytotron or greenhouse being used for hybrid seed production, a cross-incompatible inbred maize plant containing the previously described TCB trait.

Other objects, advantages and features of the present invention will become apparent from the following specification when taken in conjunction with the accompanying drawings.

BRIEF DESCRIPTION OF THE FIGURES

FIGS. 2A–2F shows ears from crosses designed to distinguish between teosinte-derived incompatibility genes segregating in W22 backcross progeny. Pollen from a colorless kernel, true breeding TCB strain was mixed with ga1 tcb1 pollen that confers kernel color and then placed on silks of plants in the test strain (See FIGS. 2A and 2D). Pollen from each of the test plants was used in crosses to Ga1-s (FIGS. 2B and 2E) and Tcb1 (FIGS. 2C and 2F) silks. Two classes of plants were present. The first class of plants are shown in FIG. 2A–FIG. 2C whose silks did not discriminate against the colored tracer pollen and whose pollen was unreceptive on both testers. These plants lack both Ga1 and Tcb1. The second class of plants were those plants shown FIG. 2D–FIG. 2F whose silks were unreceptive to the tracer pollen and whose own pollen was poorly receptive on the Ga1-s tester but receptive on Tcb1. These plants lacked Gal but carried Tcb1.

FIGS. 5A–5B shows shows Tcb1 and Gal pollen competition.

INTRODUCTION

The present invention relates to a teosinte crossing barrier ("TCB") trait. Plants containing this trait exhibit the phenotype of cross-incompatiblity. The present invention also relates to new cross-incompatible plants, including inbred, hybrid, haploid, apomictic and genetically engineered plants, containing the teosinte crossing barrier trait. The cross-incompatible plants containing the teosinte crossing barrier trait described herein can be used in commercial fields to prevent the indiscriminate hybridization of these plants from undesired lines, such as from genetically engineered plants.

Definitions

The headings provided herein are not limitations of the various aspects or embodiments of the invention which can be had by reference to the specification as a whole. Accordingly, the terms defined immediately below are more fully defined by reference to the specification as a whole.

As used herein, the term "allele(s)" means any of one or more alternative forms of a gene, all of which alleles relate to one trait or characteristic. In a diploid cell or organism, the two alleles of a given gene occupy corresponding loci on a pair of homologous chromosomes.

As used herein, the term "corn" means any variety, cultivar or population of Zea mays L.

As used herein, the term "cross-incompatibility" refers to the inability of two strains or species to hybridize and/or cross-pollinate.

As used herein, the term "elite" means a plant or variety possessing certain favorable traits, such as, but not limited to, high yield, good grain quality and disease resistance.

As used herein, the term "expressed sequence tag" or "EST" means partial gene sequence data of a cDNA clone which provides a sequence tag for a gene.

As used herein, the term "gene cluster" refers to an identified chromosomal region containing genetic material (such, as, but not limited to one or more genes or alleles) which expresses a desired trait.

As used herein, the term "heterozygous" means a genetic condition existing when different alleles reside at corresponding loci on homologous chromosomes.

As used herein, the term "homozygous" means a genetic condition existing when identical alleles reside at corresponding loci on homologous chromosomes.

As used herein, the term "hybrid" means any offspring of a cross between two genetically unlike individuals (Rieger, R., A Michaelis and M. M. Green, 1968, A Glossary of Genetics and Cytogenetics, Springer-Verlag, N.Y.).

As used herein, the terms "hybridize" or "hybridization" refers to the formation of offspring between different or unlike parents.

As used herein, the term "inbred" means a substantially homozygous individual or variety.

As used herein, the term "introgressed" means the entry or introduction of a gene or gene cluster from one plant into another. As used herein, the term "introgressing" means entering or introducing a gene or gene cluster from one plant into another.

As used herein, the term "isozyme" means detectable variants of an enzyme, the variants catalyzing the same reaction(s) but differing from each other, for example, in primary structure and/or electrophoretic mobility.

As used herein, the term "locus" or "loci" means the site in a linkage map or on a chromosome where the gene for a particular trait is located. Any one of the alleles of a gene may be present at this site.

As used herein, the term "maize" means any variety, cultivar or population of Zea mays L.

As used herein, the term "map unit" means a unit of distance in a chromosome map (linkage map), frequently measured in centiMorgans. Specifically, a mapping unit is the distance between two linked gene pairs where 1 percent of the products of meiosis are recombinant.

As used herein, the term, "microsatellite" or "simple sequence repeat (SSR) or "dinucleotide repeat" or "trinucleotide repeat" or "tetranucleotide repeat" all refer to stretches of DNA consisting of tandemly repeating di-, tri-, tetra-, or penta-nucleotide units. An SSR region can be as short as two repeating units, but more frequently is in excess of 8–10 repeating units. Simple sequence repeats are common in virtually all eukaryotic genomes studied and have been identified as useful tools for the study of genetic polymorphisms.

As used herein, the term "modifier gene" refers to a gene that affects the phenotypic expression of another gene.

As used herein, the term "molecular marker", includes, but is not limited to, an amplified fragment length polymorphism (AFLP), an expressed sequence tag (EST), a restriction fragment length polymorphism, (RFLP), a microsatellite (also known as a "simple sequence repeat" (SSR)),a single nucleotide polymorphism (SNP), or an isozyme marker which defines a specific genetic and chromosomal location.

As used herein, the term "plant" includes plant cells, plant protoplasts, plant cell tissue cultures from which maize plants can be regenerated, plant calli, plant clumps, and plant cells that are intact in plants, or parts of plants, such as embryos, pollen, ovules, flowers, kernels, ears, cobs, leaves, seeds, husks, stalks, roots, root tips, anthers, silk and the like.

As used herein, the term "population" means a genetically heterogeneous collection of plants sharing a common genetic derivation.

As used herein, the term "Restriction Fragment Length Polymorphism" or "RFLP" means a variation between individuals in DNA fragment sizes cut by specific restriction enzymes. Polymorphic sequences which result in RFLPs are used as markers on both physical maps and genetic linkage maps.

As used herein, the term "Single Nucleotide Polymorphism" or "SNP" refers to a point mutation that occurs in greater than 1% of the population.

As used herein, the term "variety" or "cultivar" means a group of similar plants that by structural features and performance can be identified from other varieties within the same species.

DETAILED DESCRIPTION OF THE INVENTION

The present invention relates to a teosinte crossing barrier trait ("TCB trait") for cross-incapatiblity. Cross-incompatible maize plants which contain the TCB trait (1) fail to set seed when pollinated with pollen from maize plants lacking the TCB trait but sets seed when pollinated by plants carrying the TCB trait (see rows 1–120 in Example 2) and/or (2) maintain functional pollen and set seed when pollinated by itself or causes other maize plants to set seed when pollinated by said plant. The TCB trait of the present invention can be introgressed into maize plants (such as inbred, hybrid, haploid, apomictic and/or genetically engineered plants) which do not contain this trait in order to produce new cross-incompatible maize plants containing the TCB trait (See Example 2).

Figure 1:
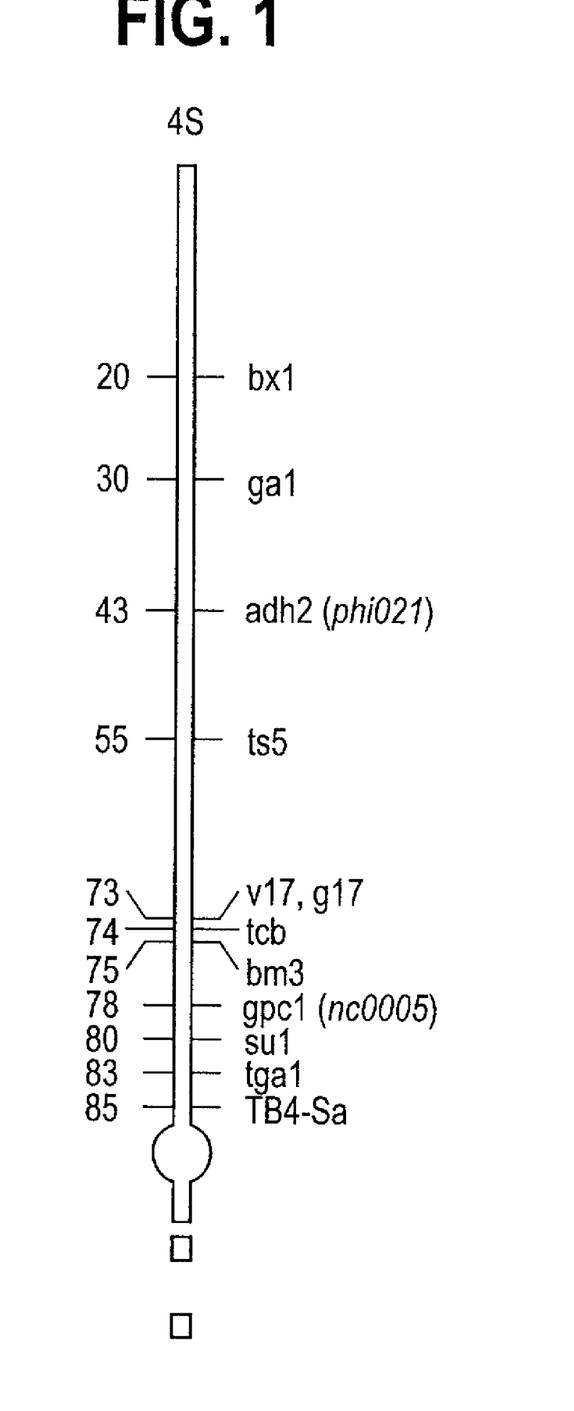
FIG. 1 shows a chromosome (linkage) map showing the location of Tcb relative to flanking genes on of the short arm of chromosome 4 in Zea mays.

The TCB trait of the present invention is comprised of a gene cluster which is expressed dominantly and located on the short arm (frequently referred to as "S") of chromosome 4, between map units 40–85 (shown in FIG. 1). Preferably, the gene cluster is located between map units 40–80 on the short arm of chromosome 4 (shown in FIG. 1 and FIG. 3B). Most preferably, the gene cluster is located between map units 66–75 on the short arm of chromosome 4 (See FIG. 3B).

The gene cluster preferably contains a locus which resides within the chromosomal position discussed previously and is referred to herein as the "teosinte crossing barrier" or "Tcb" locus. The Tcb locus is located at about 6 map units (or centiMorgans) distal to the sugary1 marker on chromosome 4S, about 40 map units (or centiMorgans) from the Ga1 marker. The Tcb locus contains genes which govern the compatibility of pollen and silks. One property encoded by at least one gene(s) comprising the Tcb locus is referred to herein as the "silk effect" function. More specifically, cross-incompatible maize plants containing the Tcb (which is either homozygous or heterozygous) and which exhibit the silk effect, when used as a female parent, fail to set seed when pollinated with pollen from maize plants which do not exhibit the TCB trait for cross-incompatibility, such as, but not limited to dent (ga1) and pop (Ga1-s) lines. Maize plants heterozygous for the Tcb locus and which exhibit the silk function, reject both ga1 and Ga1-s pollen at a level similar to the rejection of ga1 pollen by homozygous Ga1-s silks. However, while cross-incompatible maize plants containing the Tcb locus and which exhibit the silk effect, when used as a female parent, fail to set seed when pollinated with pollen from other maize plants which do not contain the Tcb locus and which do not exhibit the silk effect, such as dent (ga1) or pop (Ga1-s) corn lines, cross-incompatible maize plants containing the Tcb locus and which exhibit the silk effect, when used as a female parent, accept pollen and set seed when pollinated by maize plants containing the Tcb locus exhibiting the silk effect. The Tcb properties of a barrier to crossing, as a female parent, and the ability to overcome the barrier, as a pollen parent, are inherited together and may be functions of the same or different genes of the Tcb locus.

A second property encoded by at least one gene(s) comprising the Tcb locus is referred to herein as the "pollen effect". More specifically, maize plants containing the Tcb locus and which exhibit the pollen effect, when used as a male parent, maintain functional pollen and can fertilize themselves, as well as certain other maize plants, such as dent (gal) lines. Cross-incompatible maize plants containing the Tcb locus, and which exhibit the silk and pollen effect (a) reject pollen from dent (gal) lines when used as a female parent; and (b) maintain functional pollen and can pollinate themselves as well as dent (gal) lines, when used as a male parent.

While it is preferred herein that cross-incompatible maize plants containing the TCB trait and the Tcb locus possess at least one gene(s) encoding the silk and pollen effect functions, maize plants containing the TCB trait and the Tcb locus and possessing at least one gene(s) encoding only the silk effect or pollen effect function are also encompassed by the present invention.

In addition to the Tcb locus, the gene cluster described herein can also contain at least one modifier gene which modifies the effect of the Tcb locus. Presently, the inventors believe that at least one modifier gene which modifies the effect of the Tcb locus is located about 6.5 map units or centiMorgans from the Tcb locus in the direction of the Ga11 marker (see FIG. 1). Other modifier genes which modify the effect of the Tcb locus and which are located (1) within the gene cluster; (2) outside the gene cluster on chromosome 4; and/or (3) on one or more chromosomes other than chromosome 4, are also contemplated herein. Moreover, the gene cluster described herein may also contain other genes and such genes are also contemplated to be within the scope of the present invention.

Figure 4A:
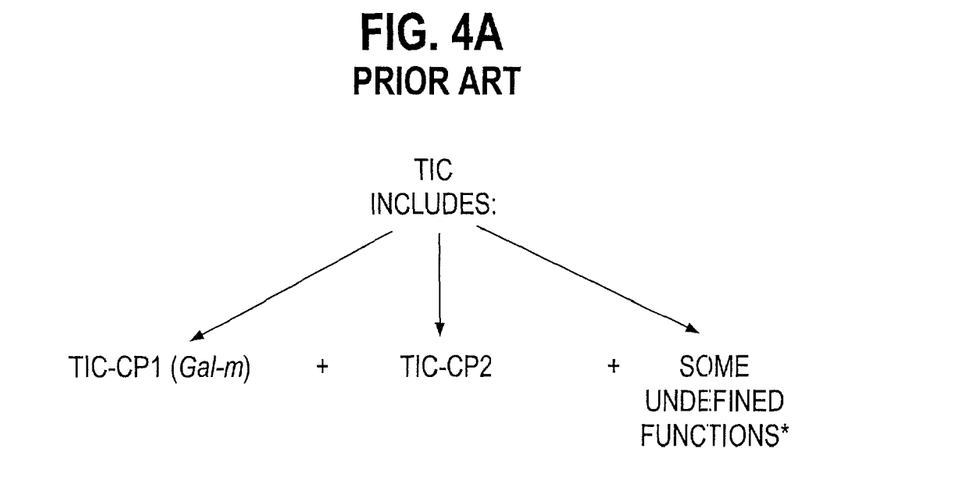
FIGS. 4A–4B shows the difference between the teosinte incompatibility ("TIC") phenotype and the TCB trait of the present invention.
Figure 4B:
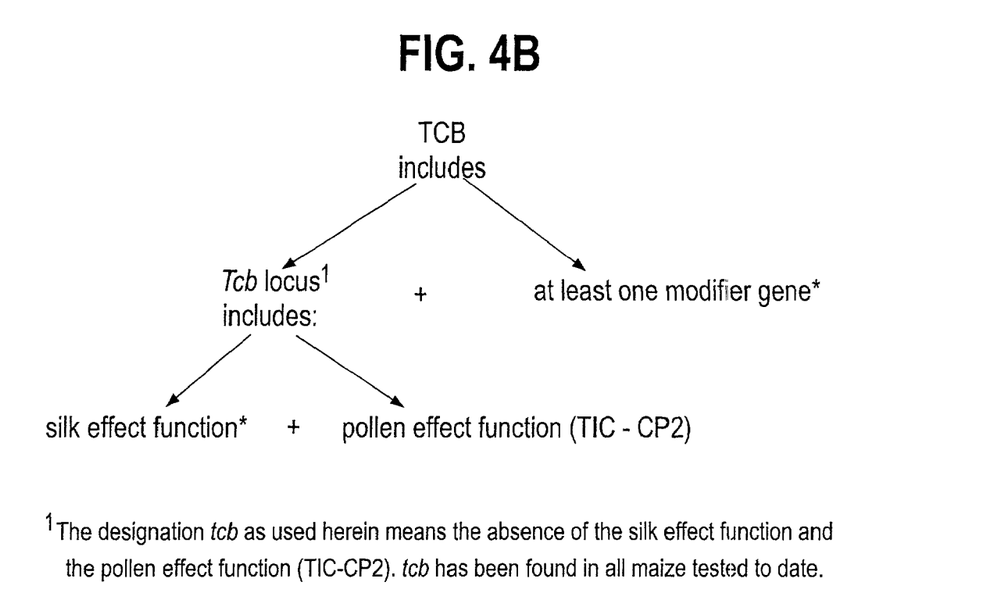

The prior art, specifically, Kermicle, J. L., et al., in *Maydica* 35:399–408 (1990) is distinguishable from the present invention in that said prior art discuses the phenotype referred to as teosinte incompatibility or "TIC". The TIC phenotype is not the same as the TCB trait. As shown in FIG. 4, the TIC phenotype discussed in Kermicle et al. is described as including TIC-CP1 (Gal-m) (which is associated with the pollen effect function Tcb), TIC-CP2 as well as some undefined functions. TIC-CP2 arose as a rare variant from TIC that lost the female function of pollen rejection. Maize plants containing TIC-CP2, when used as a male parent, were capable of pollinating maize plants containing TIC and dent (gal) but not pop (Gal-s) lines. In contrast, the present invention relates to the TCB trait. The TCB trait of the present invention includes the Tcb locus and one or more modifier genes which modify the effect of the Tcb locus. The Tcb locus of the present invention contains at least one gene(s) encoding the silk effect and/or pollen effect functions. The undefined functions generally referred to in Kermicle et al. have been discovered by the present inventors to relate to the TCB trait and comprise of one or more modifier genes and at least one gene(s) encoding the silk effect function.

An example of a maize stock which contains the TCB trait of cross-incompatiblity is dent inbred W22-TCB. Cross-incompatible inbred W22-TCB contains the gene cluster described herein. More specifically, the gene cluster contains the Tcb locus and at least one gene(s) which encode for the silk and pollen effect functions and at least one modifier gene to the Tcb locus. In addition, W22-TCB also contains TIC-CP1. Two thousand five hundred (2500) seeds of inbred line W22-TCB have been placed on deposit with the American Type Culture Collection (ATCC), 10801 University Blvd., Manassas, Va., 20110-2209 under Deposit Accession Number PTA-1601 on Mar. 30, 2000. This deposit was made in compliance with the Budapest Treaty requirements that the duration of the deposit should be for thirty (30) years from the date of the deposit or for five (5) years after the last request for the deposit at the depository or for the enforceable life of a U.S. Patent that matures from this application, whichever is longer. These seeds will be replenished should it become non-viable at the depository.

The present invention further contemplates the use of the TCB trait from dent inbred W22-TCB in crosses to develop new inbred and hybrid plants containing the TCB trait of cross-incompatibility and commercially desirable characteristics. Such new inbred and hybrid plants can be developed using plant breeding and molecular biology techniques known in art. For example, inbred W22-TCB can be used to create a first inbred dent line which is cross-incompatible and contains the TCB trait. This first inbred dent line containing the TCB trait can be crossed with a second inbred dent line to create a cross-incompatible dent hybrid having commercially desirable traits. Additionally, W22-TCB and inbreds derived therefrom can be used in anther tissue culture to create haploids and doubled haploid plants as well as apomictic maize plants. Moreover, the present invention further contemplates new maize cross-incompatible inbred, hybrid, haploid, apomictic and/or and genetically engineered plants containing the TCB trait wherein the TCB trait is derived from W22-TCB.

Molecular biology techniques can be used to identify plants which contain the TCB trait. For example, molecular markers can be used to identify the gene cluster described herein. Any molecular markers which can be used to identify the gene cluster associated with the TCB trait are contemplated as being within the scope of the present invention. For example, the markers including and between phi021 and nc005 shown in FIG. 1 and the markers including and between umc 1117 and bnlg 490, particularly, mmc0471 shown in FIG. 3B, can be used to identify the gene cluster. Thereupon, between deposited dent inbred W22-TCB and the molecular markers described herein, other sources of genetic material containing the TCB trait and gene cluster described herein can and will of course be located as the present invention now allows this material to be identified using routine techniques known in the art. More specifically, the TCB trait and gene cluster described herein can be used to identify said TCB trait or an analogous trait and analogous genes, gene clusters and/or molecular markers in other cross-pollinating monocotyledonous and dicotyledonous plants, such as, but not limited to rapeseed and rye, using techniques known in the art. The identification of homologous cross-incompatibility systems which function in a manner similar to the cross-incompatibility system described herein in maize are particularly important in rapeseed. Rapeseed is a cross-pollinating species (rapeseed contains a self-incompatibility system which prevents it from self-pollinating with itself). Unfortunately, reports of contamination of non-GM rapeseed varieties with transgenes from GM rapeseed varieties is known in the art. The development of cross-incompatible rapeseed which function similar to the cross-incompatible maize plants described herein would be beneficial to prevent the undesired and indiscriminate hybridization of rapeseed by GM rapeseed varieties.

The TCB trait described herein can be introgressed into maize plants using plant breeding techniques known in the art. Specifically, maize plants exhibiting the TCB trait herein, can be crossed as the pollen parent with other donor maize plants containing genes which encode for commercially desirable traits to create cross-incompatible inbred, hybrid, haploid, apomictic and/or and genetically engineered maize plants containing the previously described TCB trait. Cross-incompatible inbred maize lines containing the TCB trait within their genome when crossed with a second inbred maize line, can be used to produce a hybrid maize plant which is cross-incompatible and contains the TCB trait. Such cross-incompatible inbred maize plants can be developed by selecting a first donor parental maize plant from a population of maize plants which is cross-incompatible and contains the TCB trait. When a suitable donor parental maize plant containing the TCB trait is identified, it is crossed with a second donor parental maize plant. The second donor parental maize plant may or may not be cross-incompatible and contain the TCB trait. In addition, the second donor parental maize plant preferably containing genes which encode for commercially desirable traits in hybrid combination. Such commercially desirable traits include, but are not limited to, insect resistance (such as, but not limited to, resistance to mites, aphids, beetles, spiders, etc), nematode resistance (such as, but not limited to, resistance to Fall Armyworm, Western Rootworm, etc.), resistance to disease (such as, but not limited to, resistance to Northern Leaf Blight, Southern Leaf Blight, Southern Rust, Stewart's Wilt, Corn Lethal Necrosis, Head Smut, Maize Chlorotic Dwarf Virus, Maize Chlorotic Mottle Virus, Maize Dwarf Mosaic Virus, etc.), etc. The resulting seeds are collected, planted and grown under plant growth conditions. The resulting plant population is then screened for those plants which contain the previously described TCB trait. These plants are then selected for further crossings under self-pollinating or sib-pollinating conditions until an inbred line is obtained which is homozygous for the TCB trait. This cross-incompatible inbred maize line can then be used in selling, backcrossing, hybrid production, crosses to populations, and the like.

For example, an inbred maize line containing commercially desirable characteristics (the recurrent parent) can be crossed to a donor inbred (the non-recurrent parent) that carries the TCB trait described herein within its genome. The progeny of this cross is then mated back to the recurrent parent. Selections are made from the resulting progeny for those plants containing the TCB trait of cross-incompatability to be transferred from the non-recurrent parent. After three, preferably four, or more preferably five or more generations of backcrosses with the recurrent parent with selection for cross-incompatability, the progeny will be heterozygous for loci controlling the TCB trait of cross-incompability, but will be like the recurrent parent for most or almost all other genes.

Various laboratory-based techniques, such as marker-assisted selection and other techniques known in the art, can be used in backcrosses to identify the progenies having the highest degree of genetic identity with the recurrent parent. This allows for the production and identification of inbred maize lines having at least 90%, preferably 95%, and more preferably at least 99% genetic identity with the recurrent parent.

The cross-incompatible inbred maize lines described herein can be used in additional crossings to create cross-incompatible hybrid plants. For example, a first cross-incompatible inbred maize plant containing the TCB trait in its genome can be crossed as the pollen parent with a second inbred maize line. Preferably, the second inbred maize line possesses commercially desirable traits such as, but not limited to, insect resistance (such as, but not limited to, resistance to mites, aphids, beetles, spiders, etc), nematode resistance (such as, but not limited to, resistance to Fall Armyworm, Western Rootworm, etc.), resistance to disease (such as, but not limited to, resistance to Northern Leaf Blight, Southern Leaf Blight, Southern Rust, Stewart's Wilt, Corn Lethal Necrosis, Head Smut, Maize Chlorotic Dwarf Virus, Maize Chlorotic Mottle Virus, Maize Dwarf Mosaic Virus, etc.), etc. In addition, this second inbred maize line may or may not contain the TCB trait for cross-incompatibility. The resulting seed is then collected, planted and grown under plant growth conditions. The resulting plant population is then screened for hybrid plants containing the TCB trait for cross-incompatibility. These cross-incompatible hybrid plants exhibiting the TCB trait are then selected.

The cross-incompatible maize plants containing the TCB trait described herein can be used to control hybridization in a field and/or phytotron or greenhouse for the purpose of developing new inbred or a hybrid maize plants. Specifically, the cross-incompatible maize plants of the present invention can be planted in a field and/or phytotron or greenhouse and used to create new inbred and hybrid maize plants having certain commercially desirable traits without concern that these maize plants will be indiscriminately hybridized and contaminated by pollen from unwanted maize sources (such as GM maize plants) located either in the same field or in a nearby field or in the same phytotron or greenhouse. For example, cross-incompatible inbred maize plants containing within their genome the TCB trait described herein can be planted in a field and/or phytotron or greenhouse being used for hybrid seed production. These cross-incompatible inbred maize plants may be planted in or next to a field or in the same phytotron or greenhouse containing GM maize plants. These cross-incompatible maize plants can then be crossed to produce hybrid seed. Because the inbred maize plants are cross-incompatible, they will not be fertilized by any pollen originating from the GM maize plants. Instead, these plants will only be fertilized by pollen originating from a cross-incompatible maize plant containing the TCB trait described herein.

By way of example, but not limitation, examples of the present invention shall now be given.

EXAMPLE 1

Identification and Characterization of the Teosinte Crossing Barrier Locus

Example 1a

Materials and Methods

Table 1 below lists the incompatibility stocks used and gives their compatibility relations.

TABLE 1

Incompatibility Stocks

| Stock | Source of Incompatibility Genes | Distinguishing Features |
| --- | --- | --- |
| ga1 tcb1 | dent maize inbred W22 | Receptive to all pollen; unable to fertilize Gal-s/Gal-s or TCB/- |
| Gal-s tcb1 | White Cloud Popcorn hybrid | Homozygotes unreceptive and heterozygotes variably receptive to ga1 pollen; unable to fertilize TCB/- |
| Gal-m tcb1 | Central Plateau teosinte 48703 | Receptive to all pollen; able to fertilize Gal-s/Gal-s but not TCB/- |
| TCB haplotype | Central Plateau teosinte 48703 | TCB/- unreceptive to tcb1; fertilizes all pistil genotypes. TCB/TCB weakly self-incompatible. |
| ga1 Tcb1 | Central Plateau teosinte 48703 | Tcb1/- unreceptive or partly receptive to tcb1 depending on modifier constitution; unable to fertilize Gal-s/Gal-s |

In order to standardize the genetic background, the genes of interest were incorporated through backcrossing into the Midwestern US dent inbred W22, which lacks known incompatibility factors (ga1 tcb1). The Ga1-s counterpart line was developed by first crossing W22 with White Cloud hybrid popcorn, then backcrossing Ga1-s containing progeny to W22 for five generations before self-pollinating to establish a homozygous lineage. Incompatibility genes from Central Plateau teosinte collection 48703 (Wilkes, "Teosinte: the closest relative of maize". The Bussey Institute of Harvard University, Cambridge, Mass. (1967)) were transferred to maize first by crossing to various ga1 tcb1 stocks, as available, for five generations and then successively to W22. Selection for strong incompatability resulted in the multifactoral haplotype designated TCB, established for routine use as a Tcb1 tester after three generations of crossing to W22. Ga1-m tcb1 and ga1 Tcb1 were isolated from TIC, after additional generations of backcrossing (identified as classes B and C, respectively, in Table 3 of Kermicle et al., Maydica 35:399–408 (1990)). The experiment involving pollination first with ga1 tcb1 and then a day later with the plant's own pollen was conducted using stocks derived before incorporating TCB into inbred W22 background.

Example 1b

Tcb1 Mapping

Crossing a Tassel seed5 (Ts5) strain of Tcb1 to the chromosome 4 tester stock virescent17 (v17), brown midrib3 (bm3), sugary1 (su1) (Maize Genetics Cooperation Stock Center) and the F1 back to the recessive tester generated a 5-point testcross population for locating Tcb1 relative to the four visual markers. Only the non-sugary kernel class was characterized due to reduced viability and difficulty in classifying the virescent seedling phenotype within the sugary class. A sample of non-sugary kernels was field seeded, classified for v17, bm3 and ts5 phenotypes to identify crossover classes, then crossed reciprocally with TCB/su1 to determine Tcb1:tcb1 composition. Additional v17-Su crossover individuals were identified as virescent seedlings in a greenhouse planting, and then field transplants were classified for adult plant phenotypes and evaluated for Tcb1:tcb1. Five of the v17-Su1 crossovers were established from a progeny in which virescent expression was incompletely penetrant, hence the effective population size could not be determined. In the remaining three progenies studied, fifteen v17-Su1 crossovers were present among 237 plants, or 6.3±1.6%, which compares with 7.6±1.3% reported previously (Stinard, *Maize Gen. Coop. Newsletter* 72:79 (1998)).

Example 1c

Simple Sequence Repeat Analysis

Simple Sequence Repeat (SSR) markers were chosen that were known or suspected to map on the short arm of chromosome 4 based on data in MaizeDB. DNA was extracted from samples using the protocol described in Dellaporta in "Plant DNA miniprep and microprep: versions 2.1–2.3," *The Maize Handbook*, Freeling and Walbot (eds.) pp 522–525 (1994). PCR reactions were performed on a PTC-200 Thermal Cycler (MJ Research). The amplification conditions were the same as the "touchdown" profile of Senior et al., *Crop Sci*, 38:1088–1098 (1998) except that the last cycle was repeated 30 times instead of 20 times prior to terminating with a continuous 4° C. cycle. The 15 μL reaction mix consisted of 3 pmoles of each primer, 2.5 mM MgCl$_2$, 100 μM each dNTP, 10 mM Tris pH 9, 50 mM KCl, 0.1% Triton X-100, 1 mg/mL purified BSA (New England Biolabs), 0.6 units Taq DNA polymerase (Promega), and approximately 30 ng template DNA. After amplification, three μL of loading dye (30% glycerol., 0.25% bromophenol blue, 0.25% xylene cyanol) was added to each sample, and six μM of each mix was electrophoresed on 4% Metaphor (FMC Bioproducts) agarose gels in 1X TBE (Sambrook et al., *Molecular cloning: A Laboratory Manual*. Cold Spring Harbor Lab Press, New York 1989). After electrophoresis, gels were stained in 0.5 μg/mL ethidium bromide and visualized on an UV transilluminator. Allelic constitution was first determined for the v17 bm3 sul multiple tester and the Ts5 Tcb1 stock for all of the SSR markers. Those with detectable polymorphisms between the two parental types were then tested on the recombinants between Ts5 and su1.

Example 1d

Pollen Mixtures

In tests for preferential usage, approximately equal quantities of ga1 tcb pollen and that of either Ga1-s tcb1 or ga1 Tcb1 were thoroughly mixed and distributed to silks of various genotypes. The ga1 tcb source used confers colored kernels (R-sc plus other complementary genes required for aleurone color) whereas the remaining strains confer colorless kernels (r-g plus complementary color genes). For each mix, the proportion of viable pollen of the two classes was determined from the proportion of colored to colorless kernels obtained in crosses to colorless ga1 tcb (two crosses per mix). Values ranged from 28.8 to 54.2% colored. To standardize results across mixes, the proportion of colored kernels was divided by that determined for the two colorless ga1 tcb females, then averaged across the eight mixes made for each type. This transformation expresses results for the test females relative to ga1 tcb. Thus, if there is no difference in preference among pollen classes the expected value is one, or 100%. Ears having fewer than 50 kernels total were excluded from the calculation. Of the 144 crosses attempted in this experiment, 16 failed as anticipated because neither class of pollen was compatible with the pistil genotype, and four were unsuccessful for reasons extraneous to compatibility. Percentage seed set was estimated as described in Kermicle et al., *Maydica* 35:399–408 (1990).

Example 1e

Results

Three features of teosinte-derived incompatibility by Tcb1 were followed in a segregating testcross population. As female parent, plants containing Tcb1 discriminate against Tcb1 pollen (see FIG. 2). As male parent, Tcb1 pollen not only functions preferentially on Tcb1-containing silks but also is discriminated against on tcb1/tcb1 silks. Table 2 below presents data testing inheritance of these features relative to one another and in relation to four visual marker loci located in the proximal region of chromosome arm 4S. This region was chosen as likely to be of interest because only three percent sugary-1 kernels had been recovered in F2 progenies of TIC Su1/+su1 heterozygotes (Kermicle et al., *Maydica* 35:399–408 (1990)).

TABLE 2

Location on maize chromosome arm 4S of Teosinte crossing barrier1 (Tcb1) relative to four visual markers, based on a testcross population produced by crossing Ts5 V17 Bm3 Su1 (Tcb1)/ ts5 v17 bm3 su1 (tcb1) heterozygotes to ts5 v17 bm3 su1 females. Recombinant progeny grown from nonsugary kernels were evaluated for Tcb1 through reciprocal crosses with TCB Su1/+su1 and by crossing to homozygous su1

| Recombinant class | | No. plants | % seed set with recombinant class as male | % sugary kernels with recombinant class as female | % sugary kernels in crosses to su1/su1 females (no. of plants) | Tcb1:tcb1 constitution |
|---|---|---|---|---|---|---|
| I. | ts5 - V17 | 6 | 70.8 | 3.8–21.9 | 54.5 (4) | Tcb1 |
| II. | v17 - Bm3 | | | | | |
| | Group A | 4 | 66.3 | 4.2–19.2 | 57.8 (3) | Tcb1 |
| | Group B | 5 | 0.0$^a$ | 28.1–35.3 | 50.3 (4) | tcb1 |
| III. | bm3 - Su1 | 11 | 0.0$^b$ | 24.9–34.0 | 50.5 (7) | tcb1 |

$^a$zero kernels
$^b$a total of 8 kernels

Figure 3A:
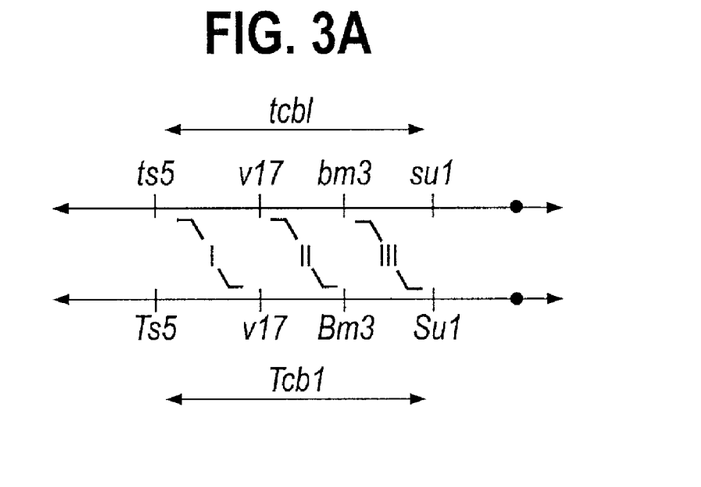
FIG. 3A shows the F1 heterozygous genotype giving parental and recombinant classes I, II and III used to located tcb.

The backcross data are summarized according to single crossover classes, no multiple crossovers having been detected. A sample of six plants recombinant for ts5 and v17 (see region I of FIG. 3A) retained all three Tcb1 features. Conversely, eleven bm3-Su1 crossovers (region III) retained none. The nine v17-Bm3 crossovers (region II) fell into two classes: four retained all Tcb1 features whereas five retained none. The regular cosegregation of the three features defines the teosinte crossing barrier1 locus. Being approximately midway between v17 and bm3, it maps to position 74 (see FIG. 3B) on the 1995 maize genetic map of Neuffer et al., *Mutants of Maize*, Cold Spring Harbor Lab Press, New York (1997).

Figure 3B:
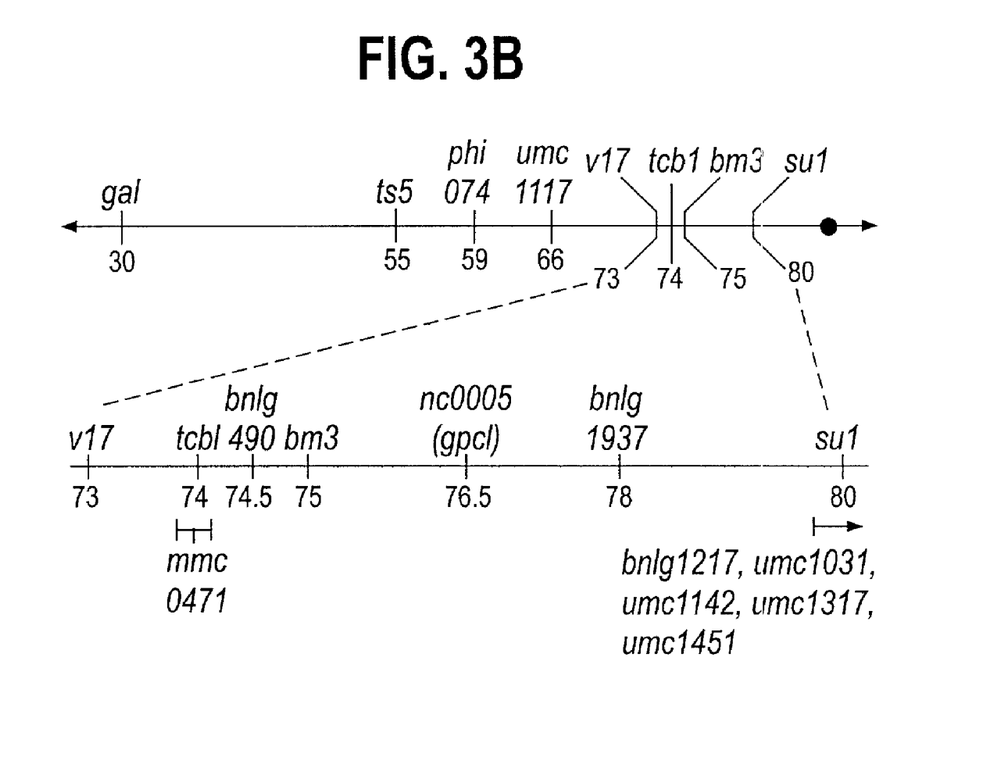
FIG. 3B shows a chromosome 4 genetic map indicating location of tcb1 relative to visual and molecular markers in the proximal region of the short arm. The centromere is indicated by a filled circle.

Simple Sequence Repeat (SSR) markers polymorphic between the multiple tester and the Ts5 Tcb1 parent were tested retrospectively on the recombinants in the four regions between Ts5 and Su1 defined by the visual markers and Tcb1 (See FIG. 3B). This data places umc1117 and phi074 distal to Tcb1 between v17 and Ts5, bnlg490 proximal to Tcb1 halfway between Tcb1 and bm3, and nc005 and bnlg1937 between bm3 and Su1. In this population mmc0471 was not separated from Tcb1.

Exclusion of tcb1 pollen by Tcb1/tcb1 plants in the foregoing linkage study was variable. Nine backcross plants of the Ts5 Tcb1 parental class produced from 1.5 to 15.3% sugary kernels rather than the Mendelian expectation of 25%. Similarly, the six ts5-V17 crossover plants ranged from 3.8 to 21.9% sugary. This compares with a range of only 1.1 to 3.8% in the reciprocal cross, for example, when pollen of the crossover plants was put onto TCB Su1/+su1 females. This lower value is in the same range of su1 kernels as when pollen of TCB Su1/+su1 males is put onto TCB Su1/+su1 females. The latter outcome, considering the 6% of recombination between tcb1 and su1 loci, is consistent with complete exclusion of tcb1 pollen. Likely explanations for attenuation of Tcb1 observed when the backcross plants were the female parent are that one or more modifier genes were lost during development of the Ts5 Tcb1 stock from TCB or that Ts5 itself dampens Tcb1 action.

A second attenuated Tcb1 strain was identified after repeated backcrossing of TCB to inbred W22. The derived Tcb1 strain was compared with TCB/+ and Ga1-s/– genotypes for ability to prevent seed set when wind pollinated with ga1 tcb1 (Table 3, below). Under condition of this test, Ga1-s/Ga1-s plants were virtually barren and even Ga1-s/ga1 heterozygotes produced less than 0.1% set. Not a single kernel set on the 47 TCB/+ plants. In contrast, a 32% set was obtained on attenuated Tcb1 homozygotes and 43% on heterozygotes. This outcome indicates that inbred W22 carries one or more modifiers that decrease effectiveness of Tcb1 in rejecting Tcb1 pollen.

TABLE 3

Average seed sets on plants differing in Ga1:ga1 and Tcb1:tcb1 constitution. Detasseled plants were allowed to wind pollinate with ga1 tcb1.

| Genotype of Female Parent | No. of Plants | Average Seed Set (%) |
|---|---|---|
| ga1 tcb1/ga1 tcb1 | 71 | 98.3 |
| Ga1-s tcb1/Ga1-s tcb1 | 43 | 0.0[a] |
| Ga1-s tcb1/ga1 tcb1 | 45 | 0.1 |
| ga1 Tcb1/ga11 Tcb1 | 42 | 31.9 |
| ga1 Tcb1/ga1 tcb1 | 45 | 42.9 |
| TCB/+ | 47 | 0.0[b] |

[a] a total of two kernels
[b] zero kernels

Separation of Tcb1 from Ga1-m, present together in the TIC haplotype, provides material suitable for testing interaction between the Ga1-s and Tcb1 incompatibility systems. To this end, ga1 Tcb1 or Ga1-s tcb1 pollen was mixed with ga1 Tcb1 and applied to silks of various incompatability genotypes. The ga1 tcb1 strain used confers colored kernels, the other strains colorless. Hence the ga1 tcb1 pollen serves as a tracer to determine how efficiently the various female parents discriminate between ga1 tcb1 and Ga1-s or Tcb1-containing pollen.

Figure 2A:
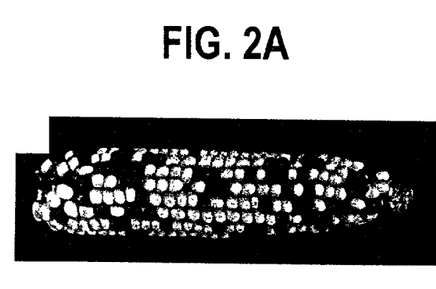
Figure 2B:
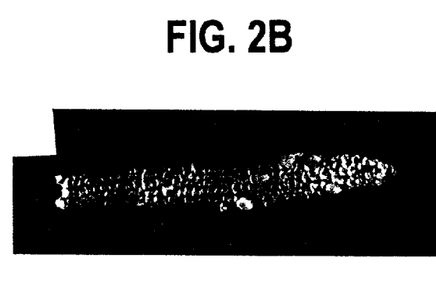
Figure 2C:
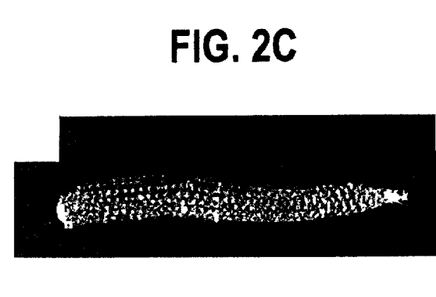
Figure 2D:
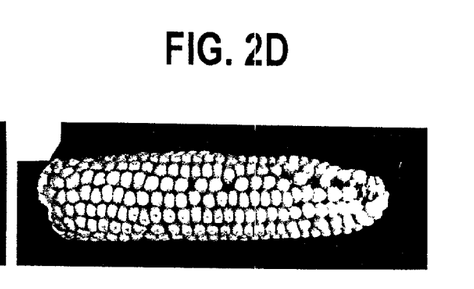
Figure 2E:
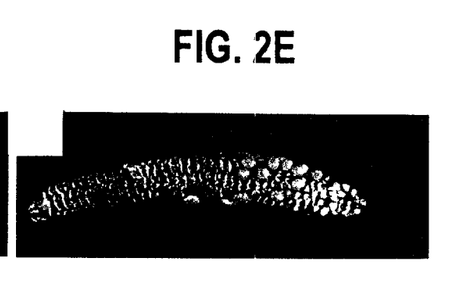
Figure 2F:
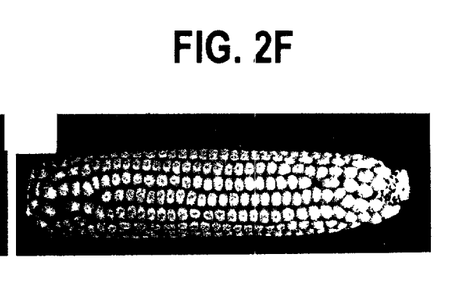
Figure 5A:
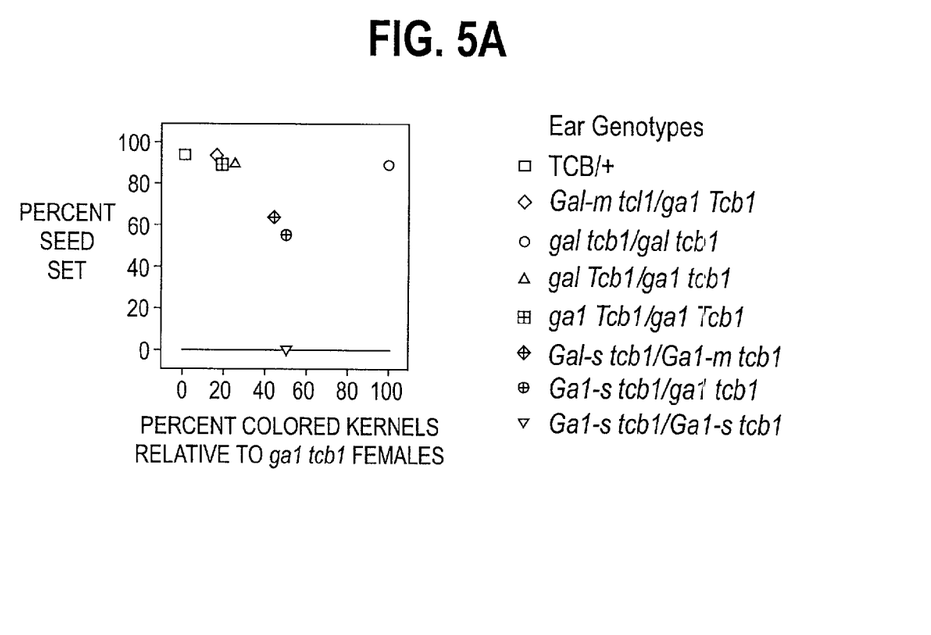
FIG. 5A shows the success of gal tcb1 pollen (colored kernel strain) in competition with gal Tcb1 (colorless kernel strain). Pollen from the two sources was mixed then placed on silks of female strains all of which confer colorless kernels.

Mixtures of ga1 Tcb1with ga1 tcb1 pollen produced essentially a full set of kernels on Tcb1-containing ear parents (FIG. 5A), as expected based on mixtures of TCB with ga1 tcb1 (FIG. 2D). TCB/+ females discriminated almost completely against ga1 tcb1 pollen, whereas attenuated Tcb1 homozygotes and heterozygotes (both homozygous ga1) averaged approximately 20% as many colored kernels as on compatible ga1 tcb1. (See Example 1 a for calibrating the proportion of viable pollen of the two classes in mixtures.) Ga1-m tcb1/ga1 Tcb1 double heterozygotes plot with the attenuated Tcb1 genotypes rather than with TCB/+. Thus the strong barrier of TCB is not due to the combination of Tcb1 with Ga1-m as such, but due to enhancement by still other factors. Homozygous Ga1-s tcb1 plants pollinated with this mixture were essentially barren. However, Ga1-s plants heterozygous with either ga1 or Ga1-m (both homozygous tcb1) produced partial sets. That there were only about half as many colored kernels as on fully compatible ga1 tcb1 shows a decided preference of Ga1-s/– pistils for Tcb1 over tcb1 pollen.

Figure 5B:
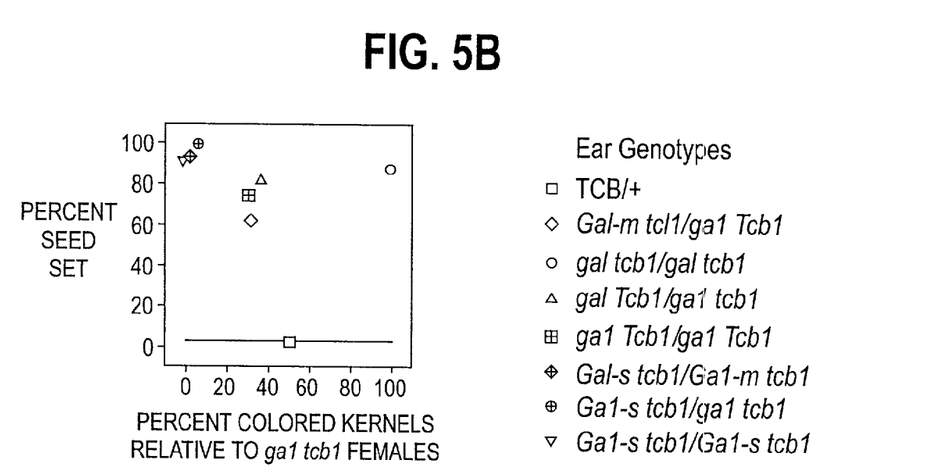
FIG. 5B shows the success of gal tcb1 pollen (colored kernel strain) in competition with Gal-s tcb1 (colorless kernel strain). Pollen from the two sources was mixed then placed on silks of the same set of female strains, all of which confer colorless kernels.

Mixtures of Ga1-s tcb with ga1 tcb pollen (FIG. 5B) produced good sets of seed on Ga1-s homozygotes and heterozygotes (all tcb1/tcb1) with almost complete discrimination against ga1 Tcb1 pollen, also as expected. TCB/+ females pollinated with the mix were almost barren, whereas attenuated Tcb1/tcb1 heterozygotes produced fairly well set ears. Neither homozygosity of the attenuated Tcb1 stock nor addition of Ga1-m caused the level of incompatibility to approach that of TCB/+. That there was a smaller fraction of colored kernels on Tcb1/– females relative to ga1 tcb1 again indicates partial cross recognition between the two incompatability systems.

Tcb1 could be expressed either before or after fertilization. If postzygotic, a reduced set of seed should accompany instances of distorted segregation, such as the deficit of sugary kernels among F2 populations of TCB/su1 heterozygotes. No reduction in set has been observed in this circumstance, providing evidence against a post-zygotic mechanism.

Conceivably, however, barrenness observed following other types of crosses could reflect postzygotic lethality. To address this possibility, ten plants in a backcross progeny segregating for heterozygous TCB and standard tcb1/tcb1 plants were pollinated on successive days. Color-marked ga1 tcb1 was applied on day one followed by the plant's own pollen on day two. Six plants produced ears with a full set of mostly colored kernels, indicating compatibility with ga1. Four plants produced mostly or only colorless and weakly colored kernels characteristic of the TCB/+ parent, indicating maintenance of ovule viability despite prior pollination with incompatible ga1 tcb1.

Example 1f

Location of a Major Modifier of Tcb Action

To locate any modifiers linked to tcb, a Ga1-m Tcb1 Su1 strain having strong Tcb action was crossed twice to ga1 Tcb1 su1. Among 62 Tcb1 carrying progeny, all but four produced 7.0% or fewer sugary kernels when self-pollinated, indicating strong Tcb1 action. The remaining four ears carried from 9.8 to 19.6% sugary, indicating loss of a modifier located approximately 6.5 centiMorgans from Tcb. That three of the four acquired ga1 from ga1 tcb1 su1 parent places the modifier proximal to Tcb1, toward ga1. This modifier evidently was removed when Ts5 was recombined with Tcb1 to produce the Ts5/Tcb1 test chromosome used to for mapping Tcb1. Its absence accounts for attenuation of Tcb1 action in the resulting stock and likewise with the strain extensively backcrossed to W22 reported in Table 3.

EXAMPLE 2

Transfer of the Teosinte Crossing Barrier Trait to Commercially Elite Hybrids and Inbred Lines Corn plants exhibiting the TCB trait prevent hybridization with certain genetic tester stocks by rejecting their pollen. This barrier to crossing can serve to isolate varieties containing TCB trait from contamination by unwanted sources of pollen. To test whether TCB would prevent pollination by commercially elite hybrids and inbred lines, hybridization experiments were conducted during the 1999/2000 winter season in test plots located on the Hawaiian island of Molokai.

As shown below in Table 4, pollen from plants of 87 different commercial and test hybrids (see rows 1–110) was placed on silks of a dent inbred W22-TCB heterozygous strain. In one attempted cross per hybrid examined to date, 74 potential ears bore no kernels, 5 ears had a single kernel and 6 ears had two kernels and 2 ears had 3 kernels. In parallel, pollen of plants representing 21 inbred lines was placed on a W22-TCB homozygous strain (containing both the Tcb locus and at least one gene(s) which encode for the silk and pollen effect functions, and modifiers to the Tcb locus in both chromosomes). This data demonstrates that the teosinte crossing barrier to crossing is effective in preventing hybridization by commercially elite inbreds and hybrids.

TABLE 4

Hawaii Nursery

| Row #[1] | Poll[2] Instruction | Entry Code[3] | Pollinator Source Row #[4] | Number of Kernels[5] | # Plant[6] | Female[7] | Male[8] | Source[9] | Notes |
|---|---|---|---|---|---|---|---|---|---|
| 1 | 0+ | 50 | 2, 3, 4, 5, 6, 10 | * | 7 | | | Jerry Kermicle | |
| 2 | 0-> | 701 | | 0 | | 4 | 5 | FFR Coop | |
| 3 | 0-> | 704 | | 0 | | 4 | 5 | FFR Coop | |
| 4 | 0-> | 705 | | 0 | | 4 | 5 | FFR Coop | |
| 5 | 0-> | 706 | | 0 | | 5 | 5 | FFR Coop | |
| 6 | 0-> | 707 | | 2 | | 5 | 5 | FFR Coop | |
| 7 | 0+ | 50 | 8, 18, 14, 15 | * | 5 | | | Jerry Kermicle | |
| 8 | 0-> | 708 | | 0 | | 5 | 5 | FFR Coop | |
| 9 | 0-> | 711 | | 0 | | 5 | 6 | FFR Coop | |
| 10 | 0-> | 712 | | 0 | | 4 | 4 | FFR Coop | |
| 11 | 0-> | 713 | | * | | 6 | 6 | FFR Coop | |
| 12 | 0-> | 716 | | 0 | | 5 | 5 | FFR Coop | |
| 13 | 0+ | 50 | 9, 12, 17 | * | 8 | | | Jerry Kermicle | |
| 14 | 0-> | 717 | | 0 | | 7 | 8 | FFR Coop | |
| 15 | 0-> | 718 | | 1 | | 9 | 9 | FFR Coop | |
| 16 | 0-> | 719 | | * | | 9 | 9 | FFR Coop | |
| 17 | 0-> | 720 | | 0, 0 | | 8 | 9 | FFR Coop | |
| 18 | 0-> | 721 | | 2 | | 9 | 9 | FFR Coop | |
| 19 | 0+ | 50 | 17, 20, 21, 22, 23, 24 | * | 8 | | | Jerry Kermicle | |
| 20 | 0-> | 723 | | 0 | | 7 | 8 | FFR Coop | |
| 21 | 0-> | 724 | | 0 | | 7 | 9 | FFR Coop | |
| 22 | 0-> | 725 | | 0 | | 7 | 9 | FFR Coop | |
| 23 | 0-> | 727 | | 0 | | 7 | 8 | FFR Coop | |
| 24 | 0-> | 728 | | 0 | | 6 | 7 | FFR Coop | |
| 25 | 0+ | 60 | 26, 27, 28, 29, 30 | * | 5 | | | Jerry Kermicle | |
| 26 | 0-> | 733 | | 0 | | 7 | 7 | FFR Coop | |
| 27 | 0-> | 734 | | 0 | | 7 | 7 | FFR Coop | |
| 28 | 0-> | 735 | | 0 | | 7 | 8 | FFR Coop | |
| 29 | 0-> | 736 | | 0 | | 7 | 8 | FFR Coop | |
| 30 | 0-> | 737 | | 0 | | 7 | 8 | FFR Coop | |
| 31 | 0+ | 60 | 32, 33, 34 | * | 3 | | | Jerry Kermicle | |
| 32 | 0-> | 738 | | 0 | | 8 | 9 | FFR Coop | |
| 33 | 0-> | 739 | | 0 | | 9 | 9 | FFR Coop | |
| 34 | 0-> | 740 | | 0 | | 8 | 9 | FFR Coop | |
| 35 | 0-> | 741 | | 0 | | 9 | 9 | FFR Coop | |
| 36 | 0-> | 742 | | 0 | | 9 | 9 | FFR Coop | |
| 37 | 0+ | 60 | 38, 39 | * | 4 | | | Jerry Kermicle | |
| 38 | 0-> | 743 | | 0 | | 7 | 7 | FFR Coop | |
| 39 | 0-> | 744 | | 1 | | 6 | 6 | FFR Coop | |
| 40 | 0-> | 745 | | 0 | | 7 | 8 | FFR Coop | |
| 41 | 0-> | 748 | | 0 | | 6 | 7 | FFR Coop | |
| 42 | 0-> | 749 | | * | | 7 | 8 | FFR Coop | |
| 43 | 0+ | 60 | 44 | * | 1 | | | Jerry Kermicle | |
| 44 | 0-> | 750 | | 0 | | 8 | 7 | FFR Coop | |
| 45 | 0-> | 751 | | 0 | | 8 | 8 | FFR Coop | |
| 46 | 0-> | 752 | | 0 | | 8 | 9 | FFR Coop | |
| 47 | 0-> | 753 | | 0 | | 7 | 7 | FFR Coop | |
| 48 | 0-> | 754 | | 0 | | 7 | 7 | FFR Coop | |
| 49 | 0+ | 50 | 50, 51, 52, 53 | * | | | | Jerry Kermicle | |
| 50 | 0-> | 903 | | 0 | | 7 | 7 | FFR Coop | |
| 51 | 0-> | 904 | | 0 | | 7 | 7 | FFR Coop | |
| 52 | 0-> | 905 | | 0 | | 7 | 7 | FFR Coop | |
| 53 | 0-> | 906 | | 0 | | 7 | 8 | FFR Coop | |
| 54 | 0-> | 907 | | 0 | | 7 | 8 | FFR Coop | |

TABLE 4-continued

Hawaii Nursery

| Row #[1] | Poll[2] Instruction | Entry Code[3] | Pollinator Source Row #[4] | Number of Kernels[5] | # Plant[6] | Flowering Data Female[7] | Male[8] | Source[9] | Notes |
|---|---|---|---|---|---|---|---|---|---|
| 55 | 0+ | 50 | 54, 56, 57, 58, 59, 60, 65, 66, 70, 71, 83, 84 | | | | | Jerry Kermicle | |
| 56 | 0-> | 908 | | 0 | | 7 | 9 | FFR Coop | |
| 57 | 0-> | 909 | | 0 | | 8 | 9 | FFR Coop | |
| 58 | 0-> | 910 | | 0 | | 8 | 9 | FFR Coop | |
| 59 | 0-> | 911 | | 0 | | | | FFR Coop | |
| 60 | 0-> | 913 | | 2 | | 7 | 7 | FFR Coop | |
| 61 | 0+ | 60 | 62, 63, 64 | * | | | | Jerry Kermicle | |
| 62 | 0-> | 914 | | 0 | | 7 | 7 | FFR Coop | |
| 63 | 0-> | 915 | | 0 | | 7 | 8 | FFR Coop | |
| 64 | 0-> | 916 | | 0 | | 9 | 10 | FFR Coop | |
| 65 | 0-> | 917 | | 0 | | 9 | 9 | FFR Coop | |
| 66 | 0-> | 918 | | 2 | | 7 | 7 | FFR Coop | |
| 67 | 0+ | 60 | 68, 69 | * | | | | Jerry Kermicle | |
| 68 | 0-> | 919 | | 0 | | 9 | 9 | FFR Coop | |
| 69 | 0-> | 920 | | 0 | | 10 | 10 | FFR Coop | |
| 70 | 0-> | 921 | | 0 | | 9 | 9 | FFR Coop | |
| 71 | 0-> | 922 | | 0 | | 8 | 10 | FFR Coop | |
| 72 | 0-> | 923 | | * | | 7 | 7 | FFR Coop | |
| 73 | 0+ | 60 | 74, 75, 76, 77, 78 | * | | | | Jerry Kermicle | |
| 74 | 0-> | 924 | | 0 | | 8 | 8 | FFR Coop | |
| 75 | 0-> | 925 | | 1 | | 6 | 7 | FFR Coop | |
| 76 | 0-> | 926 | | 0 | | 8 | 8 | FFR Coop | |
| 77 | 0-> | 927 | | 2 | | 8 | 9 | FFR Coop | |
| 78 | 0-> | 928 | | 0 | | 7 | 7 | FFR Coop | |
| 79 | 0+ | 60 | 80, 81, 82 | * | | | | Jerry Kermicle | |
| 80 | 0-> | 929 | | 0 | | 7 | 8 | FFR Coop | |
| 81 | 0-> | 930 | | 3 | | 8 | 9 | FFR Coop | |
| 82 | 0-> | 931 | | 0 | | 8 | 8 | FFR Coop | |
| 83 | 0-> | 932 | | 0 | | 7 | 8 | FFR Coop | |
| 84 | 0-> | 933 | | 0 | | 7 | 8 | FFR Coop | |
| 85 | 0+ | 60 | 86 | * | 1 | | | Jerry Kermicle | |
| 86 | 0-> | 934 | | 0 | | 7 | 9 | FFR Coop | |
| 87 | 0-> | 935 | | 0 | | 7 | 8 | FFR Coop | |
| 88 | 0-> | 936 | | 0 | | 7 | 8 | FFR Coop | |
| 89 | 0-> | 937 | | 0 | | 8 | 8 | FFR Coop | |
| 90 | 0-> | 938 | | 0 | | 7 | 7 | FFR Coop | |
| 91 | 0+ | 50 | 92, 93, 94 | * | 2 | | | Jerry Kermicle | |
| 92 | 0-> | 939 | | 0 | | 6 | 7 | FFR Coop | |
| 93 | 0-> | 940 | | 0 | | 8 | 8 | FFR Coop | |
| 94 | 0-> | 941 | | 1 | | 7 | 8 | FFR Coop | |
| 95 | 0-> | 942 | | 0, 1 | | 8 | 8 | FFR Coop | |
| 96 | 0-> | 944 | | 2 | | 6 | 7 | FFR Coop | |
| 97 | 0+ | 50 | 89 | * | 2 | | | Jerry Kermicle | |
| 98 | 0-> | 2001 | | 0 | | 6 | 6 | Renk Seeds | |
| 99 | 0-> | 2002 | | 3 | | 4 | 4 | Renk Seeds | |
| 100 | 0-> | 2003 | | * | | 4 | 5 | Renk Seeds | |
| 101 | 0-> | 2004 | | 0 | | 4 | 4 | Renk Seeds | |
| 102 | 0-> | 2005 | | 0 | | 6 | 7 | Renk Seeds | |
| 103 | 0+ | 60 | 87, 88, 90, 95 | * | 7 | | | Jerry Kermicle | |
| 104 | 0-> | 2006 | | 0 | | 5 | 6 | Renk Seeds | |
| 105 | 0-> | 2007 | | 0 | | 5 | 5 | Renk Seeds | |
| 106 | 0-> | 2008 | | 0 | | 5 | 5 | Renk Seeds | |
| 107 | 0-> | 2009 | | 0 | | 6 | 6 | Renk Seeds | |
| 108 | 0-> | 2010 | | 0 | | 5 | 6 | Renk Seeds | |
| 109 | 0-> | 60 | 95, 96, 101, 102 | * | 10 | | | Jerry Kermicle | |
| 110 | 0-> | 60 | 98, 99, 104, 105, 106, 107, 108 | * | 13 | | | Jerry Kermicle | |
| 111 | 0-> | 70 | | | 4 | | | Jerry Kermicle | |
| 112 | 0-> | 70 | | | 3 | | | Jerry Kermicle | |
| 113 | 0-> | 70 | | | 9 | | | Jerry Kermicle | |
| 114 | 0-> or 0+ | 70 | | | 8 | | | Jerry Kermicle | |
| 115 | 0-> or 0+ | 1 | | | 10 | | | Jerry Kermicle | |
| 116 | 0-> or 0+ | 1 | | | 12 | | | Jerry Kermicle | |
| 117 | 0-> or 0+ | 1 | | | 12 | | | Jerry Kermicle | |
| 118 | 0-> or 0+ | 1 | | | 18 | | | Jerry Kermicle | |
| 119 | 0-> or 0+ | 1 | | | 17 | | | Jerry Kermicle | |
| 120 | 0-> and 0+ | 3 | | | 2 | | | Jerry Kermicle | x 121, nk[10] |
| 121 | 0-> and 0+ | 2011 | Inbred A | | | | | FFR Coop, Inc. | 2 x's, x 122 (2) |
| 122 | 0-> and 0+ | 3 | | | 3 | | | Jerry Kermicle | x 123, nk |
| 123 | 0-> and 0+ | 2012 | Inbred B | | | | | FFR Coop, Inc. | x, x 159, x 122 (2), x 160 |
| 124 | 0-> and 0+ | 3 | | | 6 | | | Jerry Kermicle | x 125, nk |
| 125 | 0-> and 0+ | 2013 | Inbred C | | | 7 | 8 | FFR Coop, Inc. | 2x, x 124 (2), x 159, x 160 |

TABLE 4-continued

Hawaii Nursery

| Row #[1] | Poll[2] Instruction | Entry Code[3] | Pollinator Source Row #[4] | Number of Kernels[5] | # Plant[6] | Flowering Data Female[7] | Male[8] | Source[9] | Notes |
|---|---|---|---|---|---|---|---|---|---|
| 126 | 0-> and 0+ | 3 | | | 5 | | | Jerry Kermicle | x 127 (5), 4 nk, 1 k[11] |
| 127 | 0-> and 0+ | 2014 | Inbred D | | | | | FFR Coop, Inc. | x 160, x 159, 2x, x 126 (6) |
| 128 | 0-> and 0+ | 3 | | | 6 | | | Jerry Kermicle | x 129 (3), 2 nk, 1k |
| 129 | 0-> and 0+ | 2015 | Inbred E | | | 7 | 8 | FFR Coop, Inc. | x 128, x 159 |
| 130 | 0-> and 0+ | 3 | | | 7 | | | Jerry Kermicle | x 131, 2 nk, 1k |
| 131 | 0-> and 0+ | 2016 | Inbred F | | | | | FFR Coop, Inc. | x 159, x 160, 2x, x 130 (2) |
| 132 | 0-> and 0+ | 3 | | | 6 | | | Jerry Kermicle | x 132, 2 nk |
| 133 | 0-> and 0+ | 542 | Inbred G | B14 | | 7 | 8 | Renk Seeds | 2x, v.v.[12] |
| 134 | 0-> and 0+ | 4 | | | 3 | | | Jerry Kermicle | |
| 135 | 0-> and 0+ | 2017 | Inbred H | IODENT | | 7 | 7 | Renk Seeds | 2x, x 160, x 134 (5), x 159 |
| 136 | 0-> and 0+ | 4 | | | 4 | | | Jerry Kermicle | |
| 137 | 0-> and 0+ | 2018 | Inbred I | B14 | | 5 | 6 | Renk Seeds | 2x, failed to pollinate |
| 138 | 0-> and 0+ | 4 | | | 3 | | | Jerry Kermicle | |
| 139 | 0-> and 0+ | 2019 | Inbred J | 3737X | | 7 | 7 | Renk Seeds | 2x, x 159 |
| 140 | 0-> and 0+ | 4 | | 3 | | | | Jerry Kermicle | x 139, 1k |
| 141 | 0-> and 0+ | 2020 | Inbred K | B14 | | 7 | 7 | Renk Seeds | x160, 2x, x 159 |
| 142 | 0-> and 0+ | 4 | | | 2 | | | Jerry Kermicle | x 143, nk |
| 143 | 0-> and 0+ | 2021 | Inbred L | O43, W117 | | 6 | 6 | Renk Seeds | x 160, 2x, x 159 |
| 144 | 0-> and 0+ | 4 | | | 3 | | | Jerry Kermicle | x 145, nk |
| 145 | 0-> and 0+ | 2022 | Inbred M | | | | | Renk Seeds | x 160, 3x, x144 (2F), x 159 |
| 146 | 0-> or 0+ | 2 | | | 6 | | | Jerry Kermicle | |
| 147 | 0-> or 0+ | 2 | | | 6 | | | Jerry Kermicle | |
| 148 | 0-> or 0+ | 2 | | | 10 | | | Jerry Kermicle | |
| 149 | 0-> or 0+ | 2 | | | 6 | | | Jerry Kermicle | |
| 150 | 0-> or 0+ | 2 | | | 8 | | | Jerry Kermicle | |
| 151 | 0-> or 0+ | 2 | | | 4 | | | Jerry Kermicle | |
| 152 | 0-> or 0+ | 2 | | | 8 | | | Jerry Kermicle | |
| 153 | 0-> or 0+ | 70 | | | 4 | | | Jerry Kermicle | 35 |
| 154 | 0-> or 0+ | 70 | | | 4 | | | Jerry Kermicle | 36, 40, 41 |
| 155 | 0-> or 0+ | 70 | | | 4 | | | Jerry Kermicle | 45, 46, 47 |
| 156 | 0-> or 0+ | 70 | | | 2 | | | Jerry Kermicle | 48 |
| 157 | 0-> or 0+ | 70 | | | 2 | | | Jerry Kermicle | 182 |
| 158 | 0-> or 0+ | 70 | | | 3 | | | Jerry Kermicle | 183 |
| 159 | 0-> or 0+ | 2023 | | 4557 xgives 3%su | | | | Jerry Kermicle | |
| 160 | 0-> or 0+ | 2024 | | | | | | Jerry Kermicle | |
| 182 | 0-> and 0+ | 2046 | Inbred N | | | 7 | 7 | Curry Hybrids | nk |
| 183 | 0-> and 0+ | 2047 | Inbred N | | | 7 | 7 | Curry Hybrids | nk |
| 184 | 0-> and 0+ | 2048 | Inbred O | | | 10 | 10 | Curry Hybrids | 2x, x148, x 160 |
| 185 | 0-> and 0+ | 2049 | Inbred O | | | 10 | 10 | Curry Hybrids | x 159, x148 |
| 186 | 0-> and 0+ | 2050 | Inbred P | | | 10 | 10 | Curry Hybrids | x 159, x 148, x 160 (20k), 2x |
| 187 | 0-> and 0+ | 2051 | Inbred P | | | 10 | 10 | Curry Hybrids | x 148 |
| 188 | 0-> and 0+ | 2052 | Inbred Q | | | 7 | 7 | Curry Hybrids | 2x, 148 (nk), x 159, x 160 |
| 189 | 0-> and 0+ | 2053 | Inbred Q | | | 7 | 7 | Curry Hybrids | 2x, x 148(25x) |
| 190 | 0-> and 0+ | 2054 | Inbred R | | | 8 | 8 | Curry Hybrids | x 148, x 160(5k), 2x |
| 191 | 0-> and 0+ | 2055 | Inbred R | | | 8 | 8 | Curry Hybrids | x 148, 159 |
| 192 | 0-> and 0+ | 2056 | Inbred S | | | 8 | 8 | Curry Hybrids | x 148, 2x |
| 193 | 0-> and 0+ | 2057 | Inbred S | | | 8 | 8 | Curry Hybrids | x 159, x 160, x 148 |
| 194 | 0-> and 0+ | 2058 | Inbred T | | | 12 | 12 | Curry Hybrids | 2x, x 148, x 159 |
| 195 | 0-> and 0+ | 2059 | Inbred T | | | 12 | 12 | Curry Hybrids | 2x, x 148 |
| 196 | 0-> and 0+ | 2060 | Inbred U | | | 11 | 11 | Curry Hybrids | 2x, x 160, x 148, x 159 |
| 197 | 0-> and 0+ | 2061 | Inbred U | | | 11 | 11 | Curry Hybrids | 2x, x 148 |
| 198 | 0-> and 0+ | Sweet | | | | | | | |
| 199 | 0-> and 0+ | Sweet | | | | | | | |
| 200 | 0-> and 0+ | Sweet | | | | | | | |

[1] Row # = The order in which planted.
[2] Poll = Instruction for whether the plant was used as male or female.
[3] Entry Code = The company designation either for hybrid or inbred.
[4] Pollinator Source = Row number from which the male pollen was taken.
[5] Number of Kernels = Number of kernels that were pollinated on reciprocal test cross ears.
[6] # Plant = Number of plant stand count.
[7] Flowering Data - Female = The day in the month that silk had expressed on 50 percent of the ears on the center spike approximately 3 inches.
[8] Flowering Data - Male = The day in the month that the pollen had expressed on 50 percent of the tassels on the center spike approximately 3 inches.
[9] Source = The person and/or company that supplied the seed.
[10] nk = no kernels.
[11] k = number of kernels.
[12] v.v = viveviparity.
*= failed to pollinate.

All references cited herein are hereby incorporated by reference.

The present invention is illustrated by way of the foregoing description and examples. The foregoing description is intended as a non-limiting illustration, since many variations will become apparent to those skilled in the art in view thereof. It is intended that all such variations within the scope and spirit of the appended claims be embraced thereby.

Changes can be made to the composition, operation and arrangement of the method of the present invention described herein without departing from the concept and scope of the invention as defined in the following claims.

What is claimed is:

1. A process for obtaining a cross-incompatible inbred maize plant comprising a gene cluster that encodes for a Teosinte Crossing Barrier (TCB) trait, which when crossed with a second inbred maize plant, produces a hybrid maize plant which is cross-incompatible and contains a gene cluster that encodes for a TCB trait, the process comprising the steps of:
   a) crossing a first donor parental maize plant comprising a gene cluster that encodes for a TCB trait with a second donor parental maize plant containing genes that encode for desirable traits in hybrid combination, wherein the gene cluster in said first donor parental maize plant comprises a Tcb locus and at least one modifier gene and further wherein said first donor parental maize plant is derived from a maize plant designated W22-TCB, seeds of which have been deposited as ATCC No. PTA-1601;
   b) collecting the seed resulting from the cross in step a);
   c) planting and growing the seed collected in step b) under plant growth conditions;
   d) obtaining DNA from each of the plant of the plant population grown in step c);
   e) analyzing the DNA obtained from each plant in step d) using at least one molecular marker including and between molecular markers umc1117 and bnlg490 shown in FIG. 3B to identify a Tcb locus and at least one modifier gene;
   f) selecting plants from said population having the Tcb locus and at least one modifier gene for further crossings and screenings;
   g) repeating steps d)–f) until a line is obtained which is homozygous for the gene cluster for cross-incompatability to provide such a trait in an inbred maize plant to be used in hybrid combination; and
   h) selecting plants from said population having the gene cluster for cross-incompatibility for further crossings and screenings until a line is obtained which is homozygous for the gene cluster for cross-incompatibility to provide such a trait in an inbred maize plant to be used in hybrid combination.

* * * * *